United States Patent
Debregeas et al.

(10) Patent No.: US 6,482,437 B2
(45) Date of Patent: *Nov. 19, 2002

(54) MORPHINE SULFATE MICROGRANULES, MANUFACTURING PROCESS AND PHARMACEUTICAL PREPARATIONS

(75) Inventors: Patrice Debregeas, Paris (FR); Gérard Leduc, Malesherbes (FR); Pascal Oury, Paris (FR); Pascal Suplie, Montaure (FR)

(73) Assignee: Laboratoires des Produits Ethiques Ethypharm, Houdan (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/250,393

(22) Filed: Feb. 16, 1999

(65) Prior Publication Data
US 2002/0028246 A1 Mar. 7, 2002

(30) Foreign Application Priority Data
Feb. 16, 1998 (FR) .............................................. 98 01816

(51) Int. Cl.$^7$ ............................. A61K 9/14; A61K 9/20; A61K 9/24; A61K 9/16
(52) U.S. Cl. ...................... 424/489; 424/464; 424/471; 424/472; 424/490
(58) Field of Search ................................ 424/489, 472, 424/471, 464, 473, 480, 490; 604/890

(56) References Cited

U.S. PATENT DOCUMENTS

| | | | | |
|---|---|---|---|---|
| 4,093,708 A | * | 6/1978 | Zaffaboni et al. | |
| 4,309,996 A | * | 1/1982 | Theeuwes | |
| 4,673,405 A | * | 6/1987 | Guittard et al. | 604/890 |
| 5,411,745 A | * | 5/1995 | Oshlack et al. | 424/456 |
| 5,445,829 A | | 8/1995 | Paradissis et al. | 424/480 |
| 5,582,838 A | * | 12/1996 | Rork et al. | |
| 5,672,360 A | | 9/1997 | Sackler et al. | 424/490 |

FOREIGN PATENT DOCUMENTS

| | | |
|---|---|---|
| EP | 363 366 | 2/1995 |
| WO | WO 95/31972 | 11/1995 |

* cited by examiner

Primary Examiner—Thurman K. Page
Assistant Examiner—S. Tran
(74) Attorney, Agent, or Firm—Foley & Lardner

(57) ABSTRACT

The present invention relates to a novel oral immediate-release morphine sulfate formulation in the form of microgranules. Each microgranule comprises a neutral support grain coated with a mixture of morphine sulfate and of a binder, such as hydroxypropylmethylcellulose, which represents 10 to 50% by weight of the morphine sulfate/binder mixture. The present invention also relates to a process for the preparation of these microgranules which is carried out entirely in aqueous medium on neutral support grains. The present invention finally relates to the pharmaceutical preparations comprising the microgranules according to the invention.

17 Claims, 1 Drawing Sheet

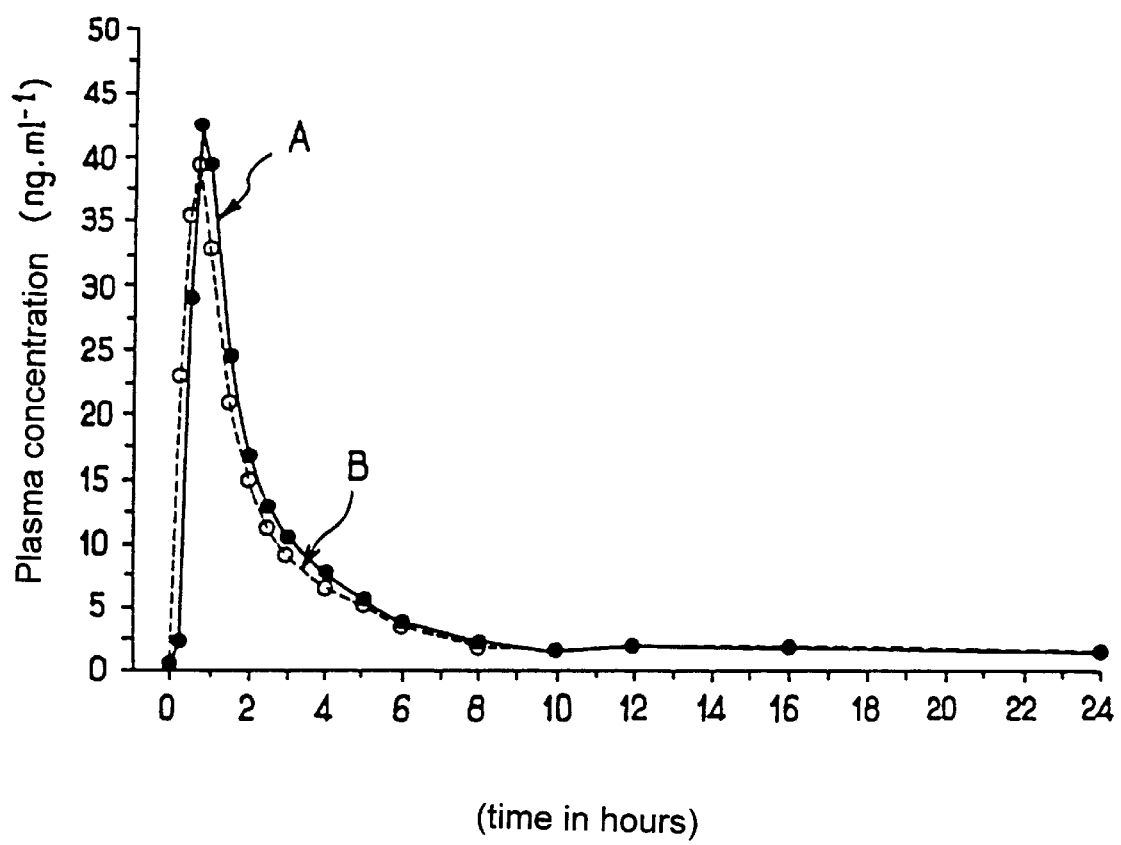

MORPHINE SULFATE MICROGRANULES, MANUFACTURING PROCESS AND PHARMACEUTICAL PREPARATIONS

The present invention relates to a novel immediate-release morphine sulfate formulation for oral administration.

In addition, the present invention applies to the process for manufacturing this formulation and to the pharmaceutical preparations comprising it.

In the present application, "morphine sulfate" is understood to mean the sulfate salt, optionally hydrated, of (5α,6α)-7,8-didehydro-4,5-epoxy-17-methyl-morphinan-3,6-diol.

In the present application, "immediate-release" is understood to mean that an active principle, in this case morphine sulfate, is made available in the body at a rate such that the plasma concentration of active principle is therapeutically effective and below the toxic concentration for a period of time of less than approximately 4 hours.

The oral administration of morphine is regarded as the treatment of choice for chronic pain.

The document EP 655,240 discloses a prolonged-release tablet comprising an immediate-release core including acetaminophen and morphine which causes the release of more than 75% of the acetaminophen in 45 minutes when it is placed in 900 ml of a 0.1N hydrochloric acid solution.

The document U.S. Pat. No. 5,445,829 discloses a formulation comprising a mixture of immediate-release particles and of delayed-release particles. The immediate-release particles are obtained by spraying a solution of binding agent over a mixture of active principle and of inert grains. The immediate-release particles comprise a binder which represents between 4 and 8% of the morphine sulfate/binder mixture.

The document U.S. Pat. No. 5,026,560 discloses granules obtained by powder spraying. These granules are composed of a neutral core coated with a mixture of active principle and of weakly substituted hydroxypropylcellulose. The binder used is an aqueous hydroxypropylcellulose solution.

The document WO 95/31972 discloses an immediate-release multiparticulate oral formulation comprising microgranules composed of a neutral core coated with a mixture of active principle, in particular morphine sulfate, and of a diluent, such as lactose hydrate, exhibiting a bulk density of between 0.4 and 0.9 g/ml. The document WO 95/31972 teaches that the binding of the morphine sulfate to neutral cores requires the addition of a diluent in order to obtain good results.

The document WO 96/00066 discloses controlled-release morphine tablets for oral administration. These tablets are obtained by successively compressing two compositions: a first so-called "therapeutic" composition obtained by wet granulation of a mixture comprising morphine sulfate, one or more poly(alkylene oxide)s and polyvinylpyrrolidone and a second composition obtained by wet granulation of a mixture comprising a poly(alkylene oxide), sodium chloride and hydroxypropylmethylcellulose. The tablet thus obtained comprises an active principle composition coated with a porous semi-permeable membrane which controls the rate of release of said active principle.

The object of the present invention is to provide an oral morphine sulfate formulation in the form of immediate-release microgranules.

The microgranules according to the invention exhibit the advantage of optimizing the distribution of the therapeutic effect by virtue of a broad distribution of the granules in the digestive tract, which contributes to a better absorption of the active principle, of avoiding the appearance of regions with a high concentration of active principle in the digestive tract, of constituting a stable formulation, of constituting a support for a prolonged-release formulation having the same pharmaceutical dosage presentation, of being able to be manufactured by a process which does not employ any organic solvent.

The immediate-release microgranules according to the invention are distinguished in that each microgranule comprises a neutral support grain coated with a mixture of morphine sulfate and of a pharmaceutically acceptable binder, such as hydroxypropylmethylcellulose, said binder advantageously representing 10 to 50% by weight of the morphine sulfate/binder mixture.

The binder preferably represents 15 to 40% by weight of the morphine sulfate/binder mixture.

The neutral support grain is composed of sucrose or of a mixture of sucrose and of starch, for example in proportions by mass of ¾. The diameter of the neutral grain is preferably between 200 and 900 microns, more preferably between 400 and 750 microns.

The microgranules are preferably coated with an outer protective layer comprising a film-forming agent, preferably hydroxypropylmethylcellulose, and optionally a lubricating agent chosen from pharmaceutically acceptable lubricants, in particular talc. The lubricating agent will advantageously be used in a proportion such that it represents 10 to 60% by weight of the binder/lubricating agent mixture.

The outer layer advantageously represents 1 to 5% by weight of the total mass of the microgranules before coating.

The content of morphine sulfate in the microgranules according to the invention is preferably between 50 and 200 mg/g.

The present invention provides immediate-release morphine sulfate microgranules which have a dissolution profile in water, buffered at a pH approximately equal to 7 and at a temperature of 37° C., by the dissolution method with a paddle at 100 revolutions/min, such that:

more than 70% by weight of active principle is dissolved after 30 minutes, more than 90% by weight of active principle is dissolved after 60 minutes.

The mean particle size of the microgranules of the invention is between 0.5 and 2 mm.

The present invention also relates to a process for the preparation of the immediate-release morphine sulfate microgranules according to the invention which is carried out entirely in aqueous medium.

The process according to the invention advantageously uses the method of emplacing on neutral support grains, in a perforated pan or in a fluidized air bed, or any other technology commonly used in the pharmaceuticals industry for the production of microgranules.

Said process comprises a stage of emplacing an aqueous suspension of morphine sulfate and of a binder on neutral support grains. This stage consists in preparing the emplacing suspension, by dissolving the binder in water and by then suspending the morphine sulfate in the solution obtained, and in then spraying the emplacing suspension over the neutral grains.

The binder is chosen from pharmaceutically acceptable binders, in particular hydroxypropylmethylcellulose.

The microgranules are optionally sieved and advantageously coated with an aqueous suspension of a film-forming agent. The suspension is obtained by dissolving in water a film-forming agent chosen from pharmaceutically acceptable film-forming agents, preferably hydroxypropylmethylcellulose.

A lubricant chosen from pharmaceutically acceptable lubricants will optionally be suspended in this protective coating solution and use will advantageously be made of talc in a proportion of 15 to 70% of the weight of dry varnish of the film-forming agent used.

The protected microgranules can be lubricated with talc and/or again sieved, before being packaged in hard gelatin capsules, in blister packs or in cases.

Another subject-matter of the present invention is the pharmaceutical preparations comprising the microgranules according to the invention, which microgranules are optionally obtained according to the process described above, in an amount equivalent to a unit dose of between 1 and 100 mg, preferably between 5 and 60 mg, more preferably between 10 and 30 mg of morphine sulfate.

The preparations according to the invention are advantageously provided in the form of hard gelatin capsules and/or of sachets which the patient can either swallow directly or mix with his meal.

The following examples illustrate the invention without limiting the scope thereof.

The single figure represents the change over time in the geometric mean of the plasma morphine concentration measured in:

30 patients to whom the microgranule formulation according to the invention has been administered in the form of hard gelatin capsules (curve A);

30 patients to whom a drinkable morphine hydrochloride formulation of the prior art has been administered (curve B).

EXAMPLE 1

Emplacing in a pan
Preparation of the active emplacing suspension

| Proportion by mass of the starting materials employed | |
|---|---|
| Morphine sulfate | 18.7% |
| Pharmacoat 603 ® | 6.5% |
| Purified water | 74.8% |

The suspension is prepared in a stainless steel receptacle. The purified water is poured into the receptacle and then stirred. The Pharmacoat 603® (manufactured by the company Shin-Etsu) is incorporated portionwise.

Stirring is maintained until the Pharmacoat 603® has completely dissolved. The morphine sulfate is incorporated portionwise.

Stirring is maintained until the active suspension is completely homogeneous and then throughout the emplacing stage.

Emplacing the active morphine sulfate suspension on the neutral support grains.

Neutres 26® support grains (manufactured by the company NP-Pharm) are placed in a rotating perforated pan. A flow of hot air is maintained through the bed of microgranules throughout the emplacing stage. The morphine sulfate is emplaced on the Neutres 26® by continuous spraying of the suspension described above.

The mass of microgranules is optionally sieved in order to guarantee the particle size homogeneity of the batch. After emplacing, a flow of unheated air is maintained through the bed of microgranules in order to bring them back to room temperature.

Preparation of the protective coating suspension
Proportion by mass of the excipients employed:

| Pharmacoat 603 ® | 9.6% |
|---|---|
| Talc | 4.7% |
| Purified water | 85.7% |

The suspension is prepared in a stainless steel receptacle. The purified water is poured into the receptacle and then stirred.

The Pharmacoat 603® is incorporated portionwise. Stirring is maintained until the Pharmacoat 603® has completely dissolved. The talc is incorporated portionwise.

Stirring is maintained until the suspension is completely homogeneous and then throughout the protective coating stage.

Protective coating of the morphine sulfate microgranules

The microgranules to be protected are placed in a rotating perforated pan. A flow of hot air is maintained through the bed of microgranules throughout the protective coating stage. Protective coating is carried out on the morphine sulfate microgranules by continuous spraying of the suspension described above. On conclusion of the protective coating, a flow of unheated air is maintained through the bed of microgranules in order to bring them back to room temperature. The mass of microgranules is optionally sieved, in order to guarantee the particle size homogeneity of the batch.

Final formula

| | Amount in % | Amount in g |
|---|---|---|
| Morphine sulfate | 15.0 | 157.5 |
| Neutres 26 ® | 75.3 | 787.1 |
| Pharmacoat 603 ® | 8.2 | 85.5 |
| Talc | 1.4 | 15.2 |
| Theoretical content | 150 mg/g | |

Dissolution of the granules in water

The granules are dissolved in 500 ml of purified water at 37° C. in a device with paddles at 100 revolutions/min.

The U.V. absorbence values are read at 285 and 310 nm.

| Time (in min) | % released as a function of time |
|---|---|
| 5' | 61.2 |
| 10' | 88.4 |
| 15' | 91.8 |
| 20' | 93.0 |
| 25' | 93.5 |
| 30' | 93.5 |
| 35' | 93.5 |
| 40' | 93.6 |
| 45' | 93.8 |
| 50' | 93.7 |
| 55' | 93.5 |
| 60' | 93.4 |

EXAMPLE 2

Emplacing in a fluidized air bed
1. The active emplacing suspension is prepared as in Example 1.
2. Emplacing of the active morphine sulfate suspension on the neutral support grains Neutres 26® support grains are placed in a fluidized air bed device.

The morphine sulfate is emplaced by continuously spraying the suspension prepared above over the Neutres 26® fluidized by a stream of hot air. The mass of microgranules is optionally sieved in order to guarantee the particle size homogeneity of the batch.

The protective coating suspension is prepared as in Example 1.

Protective coating of morphine sulfate microgranules The microgranules to be protected are placed in a fluidized air bed device.

The protective coating is carried out by continuously spraying the suspension prepared above over the morphine sulfate granules fluidized by a stream of hot air.

On conclusion of the protective coating, the granules will be maintained in the flow of hot air in order to dry them. The mass of microgranules is optionally sieved in order to guarantee the particle size homogeneity of the batch.

Final formula

|  | Amount in % | Amount in g |
| --- | --- | --- |
| Morphine sulfate | 14.7 | 138.3 |
| Neutres 26 ® | 75.8 | 713.3 |
| Pharmacoat 603 ® | 8.0 | 75.8 |
| Talc | 1.4 | 13.6 |
| Theoretical content | 147 mg/g | |

Dissolution of the granules in water

The procedure is as in Example 1.

| Time (in min) | % released as a function of time |
| --- | --- |
| 5' | 65.60 |
| 10' | 83.83 |
| 15' | 90.71 |
| 20' | 93.71 |
| 25' | 94.69 |
| 30' | 94.87 |
| 35' | 94.95 |
| 40' | 94.95 |
| 45' | 94.99 |
| 50' | 95.04 |
| 55' | 94.99 |
| 60' | 94.99 |

EXAMPLE 3

Emplacing in a fluidized air bed

The procedure is as in Example 2, the amount of protective coating being decreased.

Final formula

|  | Amount in % | Amount in g |
| --- | --- | --- |
| Morphine sulfate | 15.3 | 138.3 |
| Neutres 26 ® | 77.52 | 713.3 |
| Pharmacoat 603 ® | 6.73 | 61.9 |
| Talc | 0.73 | 6.7 |
| Theoretical content | 150 mg/g | |

Dissolution of the granules and 30 mg hard gelatin capsules in water

The procedure is as in Example 2.

| Time (in min) | (% by mass) | Hard gelatin capsules (total weight 30 mg) (% by mass) |
| --- | --- | --- |
| 5' | 67.18 | 87.84 |
| 10' | 83.57 | 97.83 |
| 15' | 90.07 | 102.55 |
| 20' | 92.85 | 104.77 |
| 25' | 93.58 | 105.44 |
| 30' | 93.80 | 105.48 |
| 35' | 93.84 | 105.28 |
| 40' | 93.80 | 105.33 |
| 45' | 93.88 | 105.38 |
| 50' | 93.92 | 105.38 |
| 55' | 93.84 | 105.43 |
| 60' | 93.83 | 105.38 |

EXAMPLE 4

Emplacing in a pan

The preparation of the active emplacing suspension and the emplacing on the neutral support grains are carried out as in Example 1.

The preparation of the protective coating suspension and the protective coating of the morphine sulfate microgranules are carried out as in Example 1 but while decreasing the amount of protective coating.

Final formula

|  | Amount in % by mass | Amount in kg |
| --- | --- | --- |
| Morphine sulfate | 15.5 | 7.6 |
| Neutres 26 ® | 76.2 | 37.2 |
| Pharmacoat 603 ® | 6.9 | 3.4 |
| Talc | 1.2 | 0.6 |
| Theoretical content | 155.7 mg/g | |

Dissolution of the granules and hard gelatin capsules in water

The procedure is as in Example 1.

|  | Granules | Hard gelatin capsules | | |
| --- | --- | --- | --- | --- |
|  |  | Total weight of 30 mg | Total weight of 20 mg | Total weight of 10 mg |
| 5' | 72.89% | 87.68% | 90.44% | 90.99% |
| 10' | 82.66% | 93.64% | 96.65% | 95.88% |
| 15' | 88.90% | 96.14% | 99.06% | 97.66% |
| 20' | 91.93% | 96.96% | 99.87% | 98.27% |
| 25' | 93.18% | 97.15% | 100.06% | 98.53% |
| 30' | 93.48% | 97.24% | 100.04% | 98.51% |
| 35' | 93.65% | 97.12% | 100.02% | 98.51% |
| 40' | 93.67% | 97.12% | 100.04% | 98.36% |
| 45' | 93.71% | 97.24% | 100.02% | 98.40% |
| 50' | 93.87% | 97.12% | 100.06% | 98.38% |
| 55' | 93.71% | 97.14% | 99.94% | 98.44% |
| 60' | 93.80% | 97.07% | 100.06% | 98.42% |

CLINICAL TRIALS

A bioequivalence study is carried out with 30 mg hard gelatin capsules, recorded as (A), with respect to a drinkable oral morphine hydrochloride formulation in the form of 0.1% phials, recorded as (B). Each phial contains 10 ml of solution, i.e. approximately 7.6 mg of morphine, whereas each hard gelatin capsule contains 30 mg of microgranules, i.e. approximately 22.5 mg of morphine.

The study is carried out as a single-blind study in a randomized way on 30 patients to whom A is administered and on 30 patients to whom B is administered.

The plasma concentrations of morphine and of 6-(glucuronide)morphine (the active metabolite) are measured by coupled high performance liquid chromatography-mass spectroscopy.

It is observed that the pharmacokinetic parameters obtained with hard gelatin capsules containing the microgranules according to the invention (A) are comparable with those obtained with phials containing dissolved morphine hydrochloride (B).

The results relating to the plasma morphine concentration are summarized in the following tables:

| Parameter | Treatment | Geometric mean | Minimum/maximum | 90% Confidence interval of the ratio of the geometric means of A/B | Optimal point in this interval |
|---|---|---|---|---|---|
| $C_{max}$ (ng.ml$^{-1}$) | A | 50 | 27/98 | 100–121 | 110 |
|  | B | 45 | 20/80 |  |  |
| $AUC_{0-\infty}$ (ng.ml$^{-1}$.h) | A | 101 | 57/161 | 102–114 | 108 |
|  | B | 94 | 56/172 |  |  |

| Parameter | Treatment | Mean of the values at $C_{max}$ | Minimum/maximum | 90% Confidence interval of the difference of the means of A and of B | Optimal point in this interval |
|---|---|---|---|---|---|
| $T_{max}$ (h) | A | 0.75 | 0.5/1 | 0.125–0.250 | 0.125 |
|  | B | 0.5 | 0.25/1 |  |  |

It is found that the optimal points of the A/B ratio for the $C_{max}$ and $AUC_{0-}$, parameters and their mutual confidence intervals lie in the 80–125% bioequivalence range.

The hard gelatin capsules comprising microgranules of the present invention are therefore bioequivalent, in terms of $C_{max}$, $AUC_{0-}$, and $T_{max}$, to the drinkable oral morphine hydrochloride formulation of the prior art.

The curves representing the change in the geometric mean of the plasma morphine concentration as a function of time for A and B are represented in the single figure.

Analogous results are obtained with 6-(glucuronide)-morphine.

The tolerances of the formulations A and B are comparable and no harmful side effect was observed.

What is claimed is:

1. An immediate-release microganule, each microgranule comprising a neutral support grain coated with a mixture of morphine sulfate and of a pharmaceutically acceptable binder, said binder representing 10 to 50% by weight of the morphine sulfate/binder mixture, and wherein said microgranule has a dissolution profile in water, buffered at a pH approximately equal to 7 and at a temperature of 37° C., by dissolution with a paddle at 100 revolutions/min, such that:

more than 70% by weight of active principle is dissolved after 30 minutes, more than 90% by weight of active principle is dissolved after 60 minutes.

2. The microgranule as claimed in claim 1, wherein the binder represents 15 to 40% by weight of the morphine sulfate/binder mixture.

3. The microgranule as claimed in claim 1, which is coated with an outer protective layer comprising a film-forming agent and optionally a lubricating agent.

4. The microgranule as claimed in claim 3, wherein the lubricating agent represents 10 to 60% by weight of the binder/lubricating agent mixture.

5. The microgranule according to claim 4, wherein the lubricating agent is talc.

6. The microgranule as claimed in claim 3, wherein the outer layer represents 1 to 5% by weight of the total mass of the microgranule before coating.

7. The microgranule as claimed in claim 3, wherein the binder and/or the film-forming agent is hydroxypropylmethylcellulose.

8. The microgranule as claimed in claim 1, wherein its content of morphine sulfate is between 50 and 200 mg/g.

9. The microgranule as claimed in claim 1, which has a mean particle size between 0.5 and 2 mm.

10. A process for the preparation of the microgranule as claimed in claim 1, which is carried out entirely in aqueous medium.

11. The process as claimed in claim 10, which comprises a stage of emplacing an aqueous suspension comprising morphine sulfate and a binder on neutral support grains in a pan or in a fluidized air bed.

12. The process as claimed in claim 11, wherein the microgranule obtained on conclusion of the emplacing stage is coated with an aqueous suspension of a film-foaming agent.

13. A pharmaceutical preparation, which comprises the microgranule as claimed in claim 1.

14. The pharmaceutical composition of claim 13, wherein said microgranule in said pharmaceutical composition is prepared in an aqueous medium comprising from 1 to 100 mg of morphine sulfate and binder of neutral support grains in a pan or in a fluidized air bed.

15. The pharmaceutical composition of claim 14, wherein said microgranule is coated with a film-forming agent.

16. The pharmaceutical composition of claim 15, wherein said film-forming agent is hydroxypropylmethylcellulose.

17. The process as claimed in claim 12, wherein the film-forming agent is hydroxypropylmethylcellulose.

* * * * *

UNITED STATES PATENT AND TRADEMARK OFFICE
CERTIFICATE OF CORRECTION

PATENT NO. : 6,482,437 B2
DATED : November 19, 2002
INVENTOR(S) : Patrice Debregeas et al.

It is certified that error appears in the above-identified patent and that said Letters Patent is hereby corrected as shown below:

<u>Title page,</u>
Item [56], References Cited, FOREIGN PATENT DOCUMENTS,
"EP 363 366" should read -- EP 636 366 --.

Signed and Sealed this

Sixteenth Day of March, 2004

JON W. DUDAS
*Acting Director of the United States Patent and Trademark Office*